US005534778A

United States Patent [19]
Loos et al.

[11] Patent Number: 5,534,778
[45] Date of Patent: Jul. 9, 1996

[54] MAGNETIC RESONANCE APPARATUS

[75] Inventors: Albertus L. J. G. M. Loos; Otto R. A. M. Selder, both of Eindhoven, Netherlands

[73] Assignee: U.S. Philips Corporation, New York, N.Y.

[21] Appl. No.: 294,286

[22] Filed: Aug. 23, 1994

[30] Foreign Application Priority Data

Aug. 24, 1993 [BE] Belgium .................. 09300866

[51] Int. Cl.⁶ ..................... G01V 3/00
[52] U.S. Cl. ............ 324/318; 128/653.5; 606/130
[58] Field of Search .................. 324/300, 318, 324/312, 314, 306, 322; 128/653.5, 653.2; 606/130

[56] References Cited

U.S. PATENT DOCUMENTS

| | | | |
|---|---|---|---|
| 5,056,523 | 10/1991 | Hotchkiss, Jr. et al. | 606/130 |
| 5,147,372 | 9/1992 | Nymark et al. | 606/130 |
| 5,155,435 | 10/1992 | Kaufman et al. | 324/309 |
| 5,242,455 | 9/1993 | Skeens et al. | 606/130 |

FOREIGN PATENT DOCUMENTS 4325206  2/1994  Germany .

Primary Examiner—Louis M. Arana
Attorney, Agent, or Firm—Jack D. Slobod

[57] ABSTRACT

Magnetic resonance apparatus includes a magnet system (1) for generating a steady magnetic field in a measurement space (29), a coil system (3) for generating gradient fields in the measurement space, and at least one RF coil (9) which is accommodated in a housing (33) which can be arranged in the measurement space and which is suitable to accommodate an object (41) to be examined, and a jig for positioning an instrument (57) introduced into the object (41). This jig has a first stop (59) for defining the position of a free end of the instrument (57) in a first coordinate direction (Z) of a three-dimensional system of coordinates. The jig also has a perforated plate (55) which is provided with holes (53) which are arranged in a matrix which extends according to second and third coordinate directions (X, Y) of the coordinate system in order to position the instrument (57) in the second and third coordinate directions. The location of a coordinate axis extending parallel to the second or the third coordinate direction (X, Y) is defined by a first phantom (71) which is rigidly arranged in the housing (33).

13 Claims, 4 Drawing Sheets

MAGNETIC RESONANCE APPARATUS

BACKGROUND OF THE INVENTION

1. Field of the Invention

The invention relates to a magnetic resonance apparatus, comprising a magnet system for generating a steady magnetic field in a measurement space, a coil system for generating gradient fields in the measurement space, and at least one RF coil which is accommodated in a housing which can be arranged in the measurement space and which is also suitable to accommodate an object to be examined, the apparatus also comprising a jig for positioning an instrument to be introduced into the object to be examined, which jig comprises a first stop for defining the position of a free end of the instrument in a first coordinate direction of a three-dimensional system of coordinates.

2. Description of the Related Art

An apparatus of this kind is known from U.S. Pat. No. 5,155,435. In the known apparatus the jig comprises a guide which is connected to the frame of the apparatus via a number of ball joints and adjustable connection means and which serves to guide the instrument which may consist of, for example a needle for carrying out a biopsy. The object to be examined, for example a part of the body of a patient, must first be introduced into the apparatus in order to form an image thereof in the absence of the instrument. This image is stored in a memory, after which the patient is removed from the apparatus. Using this image, the desired position of the instrument is determined and the jig is adjusted accordingly. Subsequently, the patient is introduced into the apparatus again; the position of the patient must be accurately the same as during the formation of the first image. Finally, using the jig, the instrument is introduced into the part of the body to be examined, it then being possible, if desired, to make a second image. This procedure is time-consuming and comparatively strenuous to the patient, because the patient must be moved into and out of the apparatus a few times. Moreover, very high requirements are imposed in respect of the accuracy with which the patient is positioned when introduced into the apparatus for the second time.

SUMMARY OF THE INVENTION

It is an object of the invention to provide a magnetic resonance apparatus of the kind set forth in which the described drawbacks do not occur. To achieve this, the apparatus in accordance with the invention is characterized in that the jig comprises a perforated plate provided with holes which are arranged in a matrix extending according to second and third coordinate directions of the system of coordinates in order to position the instrument in the second and third coordinate directions, the location of a coordinate axis extending parallel to the second or the third coordinate direction being defined by a phantom which is rigidly arranged within the housing.

Thanks to these steps, the instrument can be introduced into the object without it being necessary to remove the object temporarily from the measurement space. The position of the first phantom, and hence also the location of the second or the third coordinate axis, is clearly visible in an image formed of the object to be examined. Should the object comprise a part which must be further examined or treated by means of the instrument, therefore, the position of this part relative to the second or the third coordinate axis will also be visible. For the positioning of the instrument it is then very simple to select the correct hole in the perforated plate as well as the correct setting of the first stop.

If no further steps are taken, the resolution of positioning of the instrument according to the second and the third coordinate directions is limited by the centre-to-centre distance of the holes. In order to enable positioning also in intermediate positions, a preferred embodiment of the apparatus in accordance with the invention is characterized in that the perforated plate can be continuously displaced, relative to the housing, parallel to the second and third coordinate directions, over distances which are at least equal to the centre-to-centre distances of the holes in these directions.

For example, if the instrument is a comparatively thin needle, as used for biopsy, the diameter of the holes should be comparatively small so as to enable accurate positioning of the instrument. When the instrument is inserted into one of the holes for positioning, it could also be readily damaged. Therefore, a further embodiment of the apparatus in accordance with the invention is characterized in that the jig also comprises a holder which can be slid into each of the holes to a depth which is defined by a second stop, which holder comprises a guide for guiding the instrument in the first coordinate direction. The holder may have a comparatively large outer diameter which is substantially equal to the inner diameter of the holes, so that damaging of the instrument during positioning is prevented.

In given circumstances it may occur that the desired position of the instrument cannot be reached very well because a part of the RF coil blocks the path between the perforated plate and the desired position. Therefore, a further preferred embodiment of the apparatus in accordance with the invention is characterized in that the RF coil is mounted in the housing so that it can be displaced according to the second and/or the third coordinate direction. The RF coil can then always be displaced so that it no longer hampers the positioning of the instrument.

Evidently, it is important that the object does not move relative to the coordinate system before and during positioning of the instrument. Therefore, a further preferred embodiment of the apparatus in accordance with the invention is characterized in that the housing comprises means for immobilizing the object to be examined relative to the housing.

An embodiment of the apparatus in accordance with the invention which is particularly suitable for mammography is characterized in that the housing comprises an upper surface which extends substantially horizontally in the operating condition and which is provided with an opening at the area of the RF coil, the arrangement being such that a female patient can be arranged on the upper surface in the prone position, her breasts then hanging in the vicinity of the RF coil via the opening.

BRIEF DESCRIPTION OF THE DRAWING

These and other aspects of the invention will be described in detail hereinafter with reference to the drawing wherein.

DESCRIPTION OF THE PREFERRED EMBODIMENTS

Figure 1:
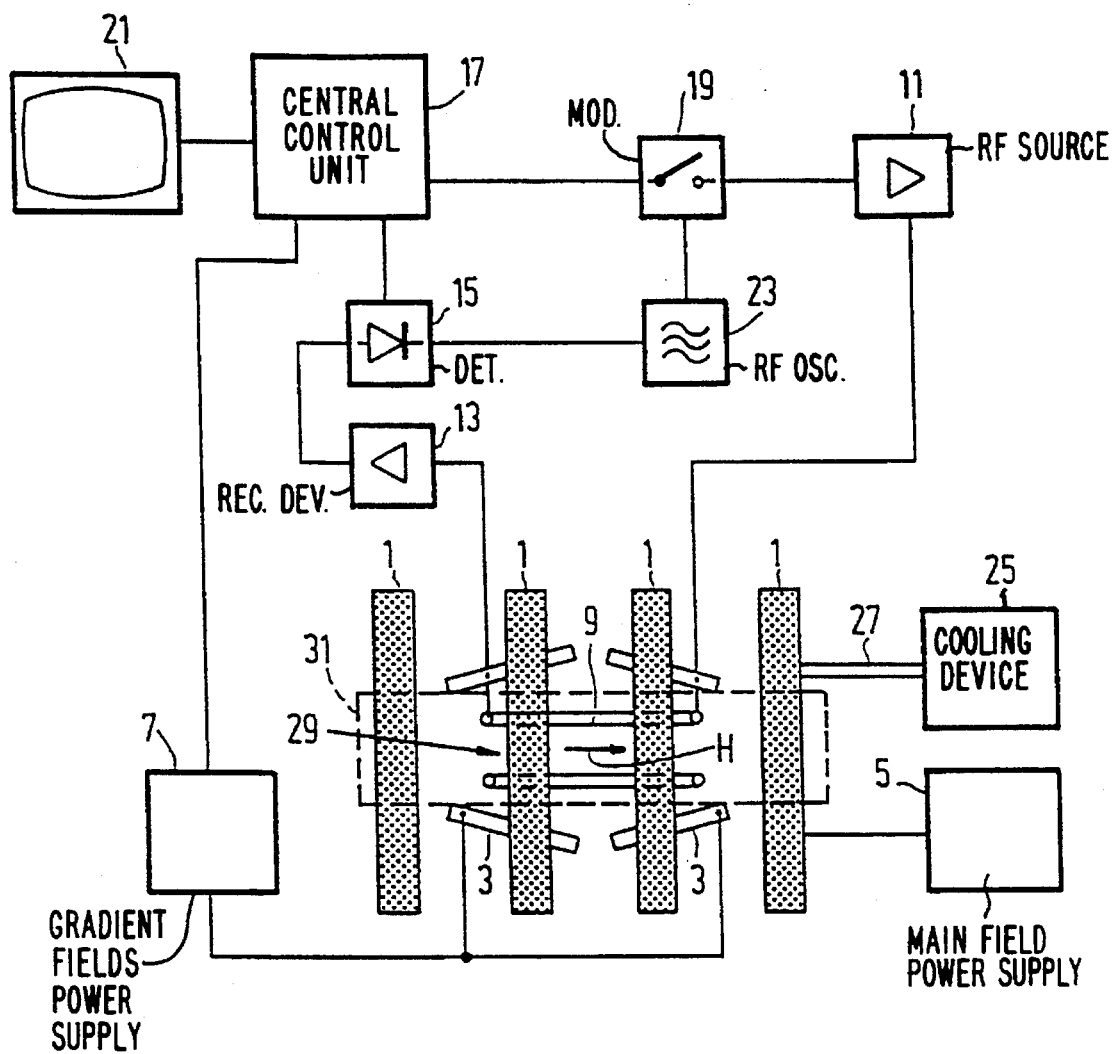
FIG. 1 shows diagrammatically an embodiment of a magnetic resonance apparatus in accordance with the invention.

The magnetic resonance apparatus which is diagrammatically shown in FIG. 1 comprises a first magnet system 1 for generating a steady main magnetic field H, a second magnet system 3 for generating magnetic gradient fields, and first and second power supply sources 5 and 7 for the first magnet system 1 and the second magnet system 3, respectively. An RF coil 9 serves to generate an RF magnetic alternating field; to this end it is connected to an RF source 11. For detection of spin resonance signals generated by the RF transmitted field in an object to be examined (not shown), use can also be made of the RF coil 9, which is then connected to a receiver device 13 for RF signals. The output of the receiving device 13 is connected to a detector circuit 15 which is connected to a central control unit 17. The central control unit 17 also controls a modulator 19 for the RF source 11, the second power supply source 7 and a monitor 21 for display. An RF oscillator 23 controls the modulator 19 as well as the detector 15 which processes the measurement signals. For cooling, if any, of the magnet coils of the first magnet system 1, there is provided a cooling device 25 which includes cooling ducts 27. A cooling device of this kind may be constructed as a water cooling system for resistive coils or, as for the high field strengths desired here, for example, as a liquid helium cooling system for superconducting magnet coils. The RF coil 9, being arranged within the magnet systems 1 and 3, generates an RF field in a measurement space 29 which, in an apparatus for medical diagnostic measurements, is spacious enough to accommodate a patient to be examined or a part of a patient to be examined. Thus, a steady magnetic field H, gradient fields selecting object slices, and a spatially uniform RF alternating field can be generated in the measurement space 29. The RF coil 9 can combine the functions of transmitter coil and measurement coil. Alternatively, different coils can be used for the two functions. Hereinafter, the RF coil 9 will be considered only as a measurement coil. If desired, the coil 9 may be enclosed by a Faraday cage 31 shielding RF fields.

Figure 2:
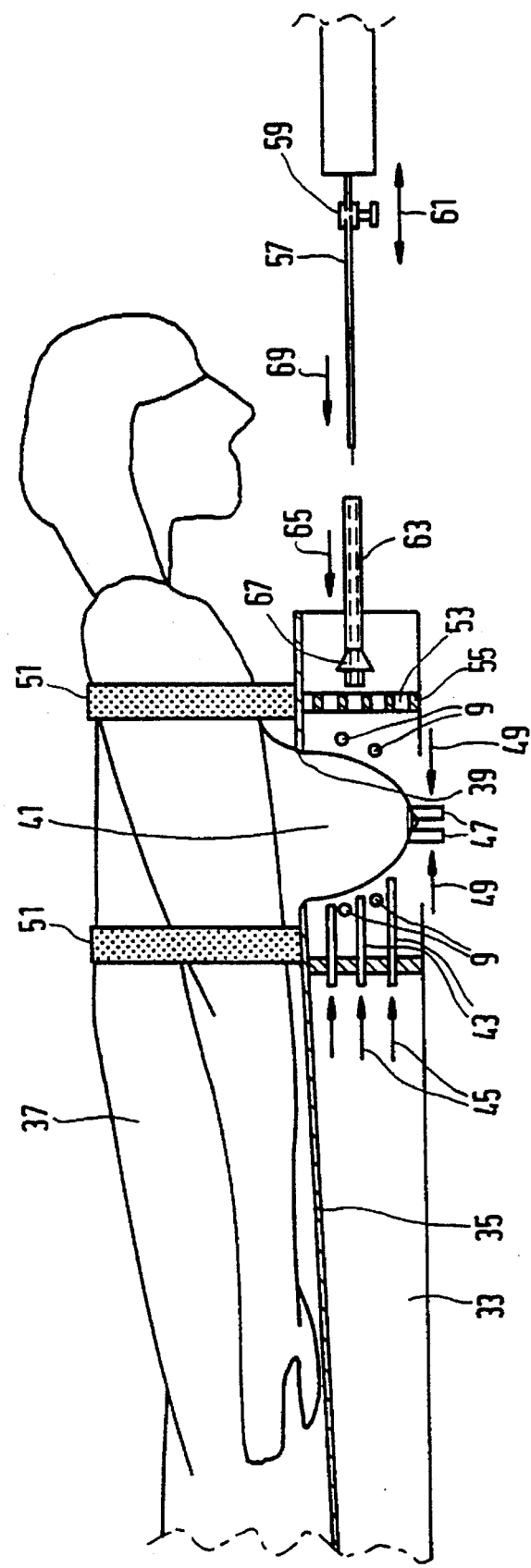
FIG. 2 is a longitudinal sectional view of a housing of an RF coil suitable for use in the apparatus shown in FIG. 1.

FIG. 2 shows an embodiment of an RF coil 9 adapted for mammography. The RF coil 9 is accommodated in a housing 33 which can be arranged in the measurement space 29. The housing 33 comprises an upper surface 35 which extends substantially horizontally in the operating condition and on which a female patient 37 can be arranged in the prone position. The upper surface 35 is provided with an opening 39 which is located so that the breasts 41 of the patient 37, one of which is visible in FIG. 2, are positioned, via this opening, in the interior of the housing 33 so as to be enclosed by the RF coil 9. Alternatively, the housing 33 may comprise a separate RF coil 9 for each breast. The housing 33 preferably comprises means for immobilizing the object to be examined, being the breasts 41 in the present example, relative to the housing. These means may be formed, for example by supporting elements 43 which can be pressed against the breast 41 in the direction of the arrows 45. Another feasible embodiment of these means is formed by a nipple clamp 47 which comprises parts which are displaceable in the direction of the arrows 49 and wherebetween a nipple can be clamped. Other possibilities, not shown in the Figure, consist in creating a pressure deficiency in the part of the housing in which the breast is situated, in providing inflatable cushions at one or more sides of the breast, or in providing a suction cup for retaining the breast. Combinations of two or more of these solutions are also feasible. In order to prevent the patient from moving during the examination, she can be immobilized by means of straps 51. Furthermore, the housing 33 accommodates a plate 55 which is provided with holes 53 and which is arranged near the RF coil 9, said plate forming part of a jig for positioning an instrument 57 to be introduced into the object 41 to be examined, for example a needle for biopsy. For example, when an image produced by means of the apparatus shown in FIG. 1 reveals a tumor in a given location within the object 41, at the area of the tumor some tissue can be removed by means of the biopsy needle 57 for further examination. To this end, the needle 57 is introduced, via one of the holes 53, into the object 41 to a depth which is defined by a first stop 59. The first stop 59 is mounted so as to be displaceable on the needle as denoted by the arrow 61. The needle 57 is preferably provided with a scale for adjustment of the correct position of the stop 59. In order to facilitate the positioning of the needle 57 in one of the holes 53, and to prevent the needle from being damaged, the jig also comprises a holder 63 which is shaped mainly as a tube whose outer diameter at the front side (at the left in FIG. 2) is substantially equal to the inner diameter of the holes 53 so that the holder fits into one of the holes substantially without play. The holder 63 can be slid into one of the holes in the direction of the arrow 65 to a depth which is defined by a second (fixed) stop 67 in the form of a thickened portion on the outer side of the holder. The holder also comprises an internal through-cavity whose diameter is substantially equal to the outer diameter of the needle 57, so that the needle is displaceable substantially without play in the holder in the direction of the arrow 69. This internal cavity constitutes a linear guide for the needle 57. The needle 57 may be arranged in the holder 63 in advance, so that only the non-vulnerable holder need be inserted into one of the holes 53 in order to position the needle. The needle 57 can subsequently be introduced into the object 41, via the holder 63, until the first stop 59 abuts against the rearmost end (at the right in FIG. 2).

Figure 3:
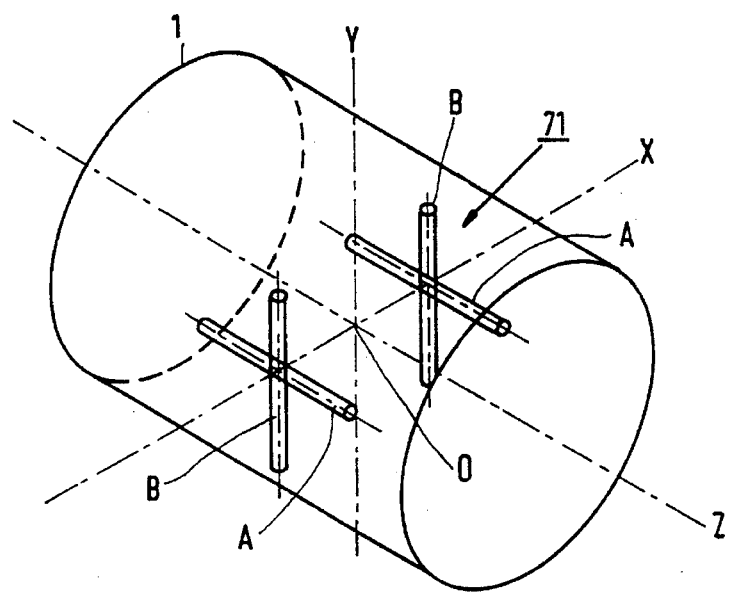
FIG. 3 shows the position of some parts of the apparatus of FIG. 1 relative to a system of coordinates.

In order to determine the hole 53 in which the holder is to be inserted as well as to determine the depth whereto the first stop 59 must be adjusted, it is first necessary to determine the position of a tumor present in the object relative to the perforated plate 55 or, more generally speaking, relative to the housing 33. To this end, a first phantom 71 is mounted so as to be stationary in the housing 33, near the RF coil 9, said phantom being shown in FIG. 3. In the present embodiment is formed the first phantom 71 by two pairs of rods A and B which cross one another at right angles, one pair being situated in front of the plane of drawing of FIG. 2 whereas the other pair is situated behind this plane of drawing. The rods A extend in the horizontal direction and the rods B in the vertical direction. The connecting line between the points of intersection of the two pairs of rods A, B defines an X-axis of a rectangular system of coordinates whose origin O is situated halfway the connecting line. The Y-axis of the system of coordinates extends parallel to the vertical rods B and the Z-axis extends parallel to the horizontal rods A. As is customary for phantoms, the rods A, B are made of a material which can be suitably reproduced by means of a magnetic resonance apparatus. FIG. 3 also shows diagrammatically the magnet system 1 which is shaped mainly as a cylinder whose axis extends according to the Z-axis of the system of coordinates. During the formation of an image by means of the apparatus, the object 41 to be examined is located between the two pairs of rods A, B. These pairs are, therefore, imaged together with the object 41 as shown in the FIGS. 4 and 5.

Figure 4:
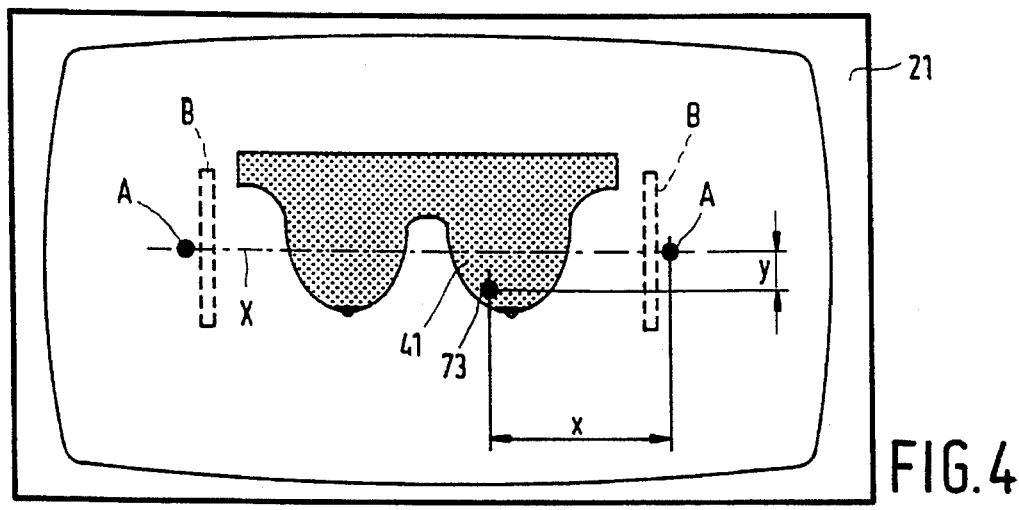
FIGS. 4 and 5 show two images which can be produced by means of the apparatus shown in FIG. 1.
Figure 5:
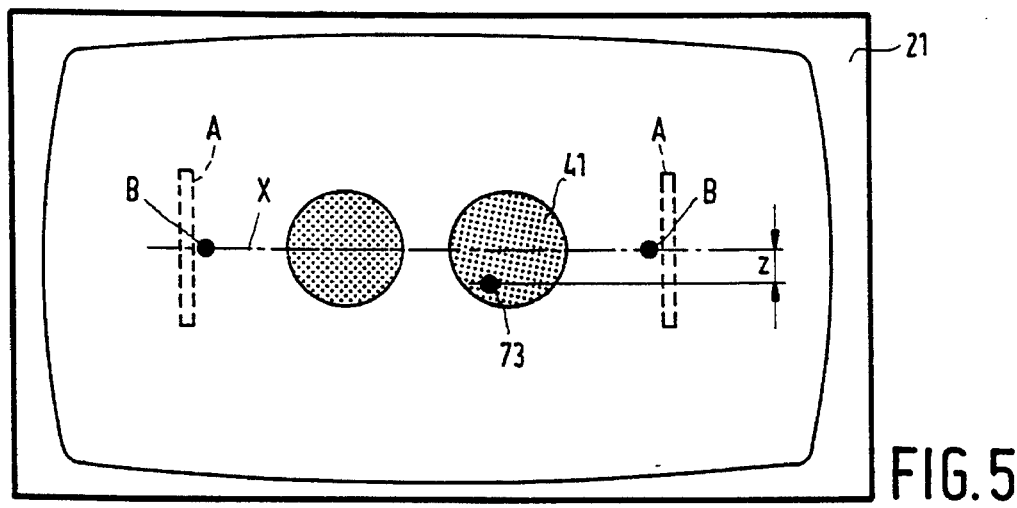

FIG. 4 shows the display screen of the monitor 21 with an image of a transversal breast scan (a cross-section in the X-Y plane of the system of coordinates) and FIG. 5 shows the display screen with an image of a frontal breast scan (a cross-section in the Z-X plane). In the image of FIG. 4 the horizontal rods A are distinct as dots, and the rods B are less clearly visible as lines. In FIG. 5, however, the rods B are visible as distinct dots and the rods A as vaguer lines. In both Figures the X-axis is shown as a dash-dot line extending between the rods A—A and B—B, which are displayed as dots. In one of the breasts 41 a tumor 73 is visible; the position of the tumor relative to the first phantom 71 can be readily determined with high accuracy. In FIG. 4 the distance y in a direction parallel to the Y-axis and the distance x in a direction parallel to the X-axis can be read relative to one of the horizontal rods A. In FIG. 5 the distance z in a direction parallel to the Z-axis can be read relative to one of the vertical rods B. The situation of the tumor 73 within the system of coordinates is thus fully determined. The position of the perforated plate 55 within the system of coordinates is also defined, so that the needle 57 can be easily positioned so that its free end reaches exactly the tumor 73.

Figure 6:
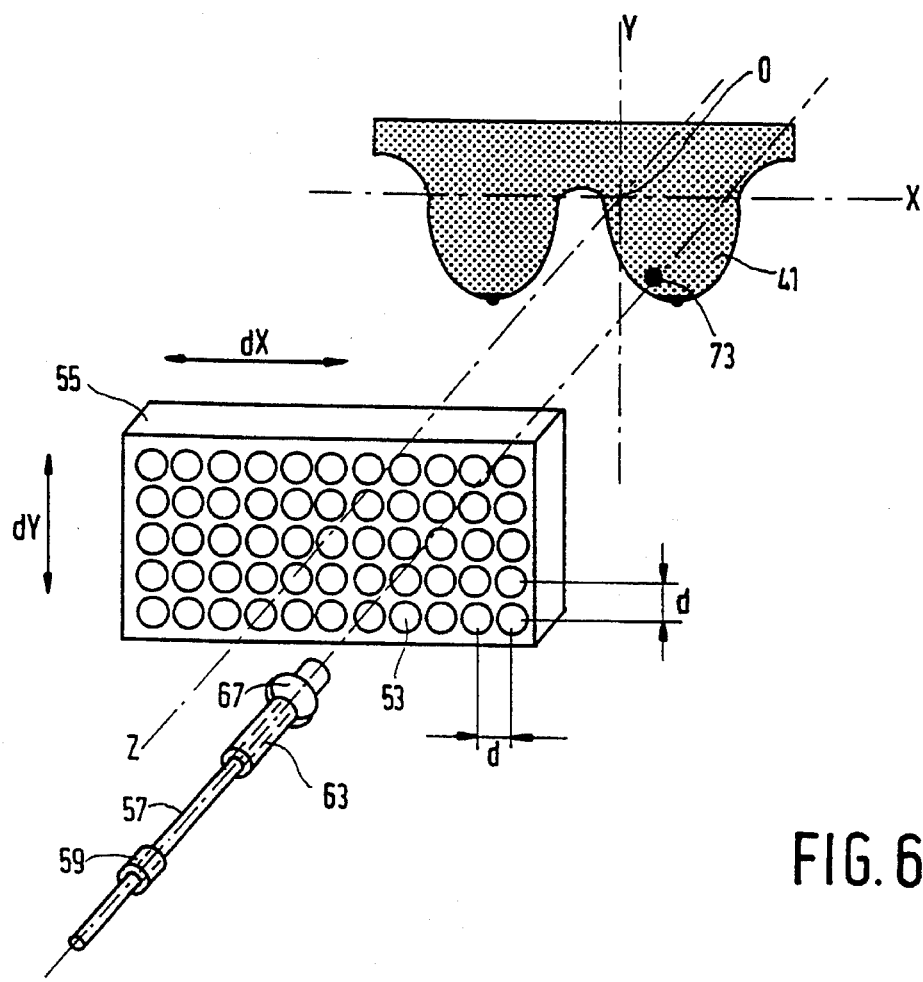
FIG. 6 is a diagrammatic exploded view of some parts of the apparatus shown in FIG. 1 and an object to be examined.

FIG. 6 illustrates the positions, relative to the system of coordinates, of the object 41 with the tumor 73 on the one side and the perforated plate 55 on the other side. The perforated plate 55 is mounted in the housing 33 so that its plane extends perpendicularly to the Z-axis and hence parallel to the X-Y plane. This means that the holes 53 are arranged according to a matrix extending along the X and Y coordinates, and that the needle 57 moves in the holder 63 in the Z-direction. The needle 57 can be simply positioned by inserting the holder 63 into a hole 53 whose X and Y coordinates correspond to the X and Y coordinates of the tumor 73, and by adjusting the first stop 59 so that the Z coordinate of the free end of the needle is the same as the Z coordinate of the tumor after the needle has been slid into the holder as far as the first stop. Because the first stop 59 can be continuously displaced in the longitudinal direction of the needle 57, the Z coordinate can be adjusted with any desired resolution. The resolution for adjustment of the X and Y coordinates, however, is limited by the centre-to-centre distance of the holes 53. This distance is denoted by the referenced in FIG. 6. In the example shown, the centre-to-centre distance equals d in the X direction as well as in the Y direction. Evidently, these distances may also be different. The resolution that can be achieved is limited by the smallest distance d permissible between the holes 53 in view of mechanical restrictions. In some cases, however, a higher resolution is desired. This problem can be solved by mounting the perforated plate 55 in the housing 33 in such a way that it can be continuously displaced in the X direction and the Y direction over distances dx and dy as shown in the Figure. A resolution which is in principle unlimited can be achieved when dx and dy are larger than d. Such mounting can be realised in known manner, for example by means of adjusting screws capable of displacing the plate against the force of a spring (not shown).

Figure 7:
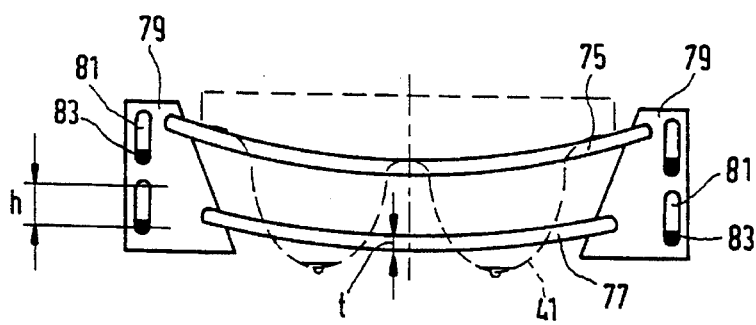
FIG. 7 illustrates a feasible method of mounting an RF coil in the housing shown in FIG. 2.

The RF coils 9 comprise electrical conductors which may be situated between the perforated plate 55 and the object 41 to be examined. Consequently, one of these conductors could constitute an obstacle hampering the movement of the free end of the needle 57 to the tumor 73. FIG. 7 shows two conductors 75 and 77 which form part of the RF coil and which extend mainly in the X direction and between the object 41 (denoted by dashed lines) and the perforated plate 55 (not visible in FIG. 7). The thickness of these conductors, including an insulating sheath, if any, is denoted by the reference t. Should the tumor 73 be situated exactly behind, for example the conductor 77, viewed from the hole 53 chosen, the tip of the needle could not reach the tumor. In order to solve this problem, the RF coil 9 is mounted in the housing 33 so that it is displaceable in the Y direction over a distance h which is preferably slightly larger than the conductor thickness t. To this end, the conductors 75 and 77 may be secured in supports 79 provided with elongate holes 81 which extend in the Y direction and wherethrough pins 83, secured to the wall of the housing 33, project (not visible in FIG. 7). The RF coil can then be displaced in the Y direction, for example by means of known adjusting screws (not shown).

Figure 8:
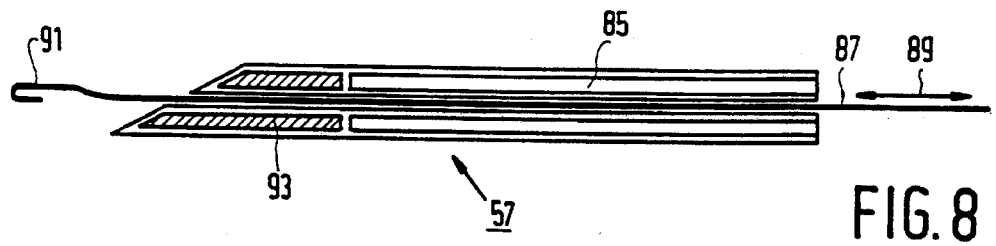
FIG. 8 is a longitudinal sectional view of an embodiment of an instrument suitable for use with the device shown in FIG. 1.

FIG. 8 shows some details of an embodiment of an instrument 57 in the form of a biopsy needle. The instrument is designed as a hollow needle 85 in which a thin rod 87 is displaceable in the longitudinal direction as denoted by a double arrow 89. At the free end of the rod them is formed a hook 91 whereby a tissue sample can be removed from the object 41 to be examined. The needle preferably comprises a second phantom 93 near its free end, which phantom contains a material which can be readily imaged by means of a magnetic resonance apparatus. The second phantom 93 can be used to check, by means of the apparatus, whether the free end is indeed situated at the area of the tumor 73 after introduction of the instrument 57. The same object can be achieved by coveting the tip of the needle with a layer of a material which can be readily imaged by magnetic resonance imaging, for example gadolinium. Another possibility consists in incorporating a small receiving coil in the tip of the needle to detect the RF field of the RF coil 9.

The described embodiment is particularly suitable for mammography. It will be evident that the invention can also be used for examination of other parts of the body, such as the head (see U.S. Pat. No. 5,155,435) or limbs. Evidently, the instrument 57 can be used for purposes other than biopsy, for example for the removal or destruction of malignant tissue. In that case the instrument 57 may be formed by a treatment needle instead of the biopsy needle, in order to treat the tumor in known manner, for example by means of a liquid, a heat source (for example, a laser), a cold source or a radioactive source.

We claim:

1. A magnetic resonance apparatus, comprising a magnet system for generating a steady magnetic field in a measurement space, a coil system for generating gradient fields in the measurement space, and at least one RF coil which is accommodated in a housing which can be arranged in the measurement space and which is also suitable to accommodate an object to be examined, the apparatus also comprising a jig for positioning an instrument to be introduced into the object to be examined, which jig comprises a first stop for defining the position of a free end of the instrument in a first coordinate direction of a three-dimensional system of coordinates, a perforated plate mounted in the housing and provided with holes which are arranged in a matrix extending according to second and third coordinate directions of the system of coordinates in order to position the instrument in the second and third coordinate directions, the location of a coordinate axis extending parallel to the second or the third coordinate direction being defined by a first phantom which is rigidly arranged within the housing, the perforated plate being mounted in the housing in such a manner that it can be continuously displaced relative to the housing, parallel to the second and third coordinate directions, over distances which are at least equal to the center-to-center distances of the holes in these directions.

2. A magnetic resonance apparatus as claimed in claim 1, wherein the jig also comprises a holder which can be slid into each of the holes to a depth which is defined by a second stop, which holder comprises a guide for guiding the instrument in the first coordinate direction.

3. A magnetic resonance apparatus as claimed in claim 2, wherein the RF coil is mounted in the housing so that it can be displaced according to the second and/or the third coordinate direction.

4. A magnetic resonance apparatus as claimed in claim 2, wherein the housing comprises means for immobilizing the object to be examined relative to the housing.

5. A magnetic resonance apparatus as claimed in claim 2, said apparatus being for performing mammography, wherein the housing comprises an upper surface which extends substantially horizontally in the operating condition and which is provided with an opening at the area of the RF coil, the arrangement being such that a female patient can be arranged on the upper surface in the prone position, her breasts then hanging in the vicinity of the RF coil via the opening.

6. A magnetic resonance apparatus as claimed in claim 2, wherein the instrument is provided near its free end with a second phantom in order to render the position of this free end detectable during an examination.

7. A magnetic resonance apparatus as claimed in claim 1, wherein the RF coil is mounted in the housing so that it can be displaced according to the second the third coordinate direction.

8. A magnetic resonance apparatus as claimed in claim 7, said apparatus being for performing mammography, wherein the housing comprises an upper surface which extends substantially horizontally in the operating condition and which is provided with an opening at the area of the RF coil, the arrangement being such that a female patient can be arranged on the upper surface in the prone position, her breasts then hanging in the vicinity of the RF coil via the opening.

9. A magnetic resonance apparatus as claimed in claim 7, wherein the instrument is provided near its free end with a second phantom in order to render the position of this free end detectable during an examination.

10. A magnetic resonance apparatus as claimed in claim 1, wherein the housing comprises means for immobilizing the object to be examined relative to the housing.

11. A magnetic resonance apparatus as claimed in claim 1, said apparatus being for performing mammography, wherein the housing comprises an upper surface which extends substantially horizontally in the operating condition and which is provided with an opening at the area of the RF coil, the arrangement being such that a female patient can be arranged on the upper surface in the prone position, her breasts then hanging in the vicinity of the RF coil via the opening.

12. A magnetic resonance apparatus as claimed in claim 11, further comprising means for immobilizing the body of the patient relative to the housing.

13. A magnetic resonance apparatus as claimed in claim 1, wherein the instrument is provided near its free end with a second phantom in order to render the position of this free end detectable during an examination.

* * * * *